(12) United States Patent
Olms et al.

(10) Patent No.: US 8,262,706 B2
(45) Date of Patent: Sep. 11, 2012

(54) DEVICE FOR CREATING A BONE IMPLANT

(75) Inventors: Kai-Hinrich Olms, Bad Schwartau (DE); Roman Nassut, Molln (DE)

(73) Assignee: Stryker Trauma GmbH (DE)

( * ) Notice: Subject to any disclaimer, the term of this patent is extended or adjusted under 35 U.S.C. 154(b) by 1070 days.

(21) Appl. No.: 12/156,951

(22) Filed: Jun. 5, 2008

(65) Prior Publication Data

US 2009/0138051 A1    May 28, 2009

Related U.S. Application Data

(60) Provisional application No. 60/959,274, filed on Jul. 11, 2007.

(51) Int. Cl.
*A61B 17/80* (2006.01)
(52) U.S. Cl. .......... 606/280; 606/286
(58) Field of Classification Search .......... 606/70, 606/105, 280, 282, 286, 288
See application file for complete search history.

(56) References Cited

U.S. PATENT DOCUMENTS

| | | | |
|---|---|---|---|
| 2,489,870 A | 11/1949 | Dzus | |
| 3,025,853 A | 3/1962 | Mason | |
| 3,489,143 A | 1/1970 | Halloran | |
| 4,185,624 A | 1/1980 | Gentile et al. | |
| 4,409,974 A | 10/1983 | Freedland | |
| 4,456,005 A | 6/1984 | Lichty | |
| 4,940,467 A | 7/1990 | Tronzo | |
| 5,122,133 A | 6/1992 | Evans | |
| 5,129,903 A | 7/1992 | Luhr et al. | |
| 5,152,794 A * | 10/1992 | Davidson | 623/23.6 |
| 5,217,462 A | 6/1993 | Asnis et al. | |
| 5,498,265 A | 3/1996 | Asnis et al. | |
| 5,722,976 A | 3/1998 | Brown et al. | |
| 6,146,384 A | 11/2000 | Lee et al. | |
| 6,302,887 B1 | 10/2001 | Spranza et al. | |
| 6,322,562 B1 | 11/2001 | Wolter | |
| 6,383,186 B1 | 5/2002 | Michelson | |
| 6,454,770 B1 * | 9/2002 | Klaue | 606/281 |
| 6,623,486 B1 | 9/2003 | Weaver et al. | |
| 6,955,677 B2 | 10/2005 | Dahners | |
| 6,974,461 B1 | 12/2005 | Wolter et al. | |
| 7,070,601 B2 | 7/2006 | Culbert et al. | |
| 2002/0143338 A1 | 10/2002 | Orbay et al. | |

(Continued)

FOREIGN PATENT DOCUMENTS

DE    4007306    5/1991

(Continued)

*Primary Examiner* — Nicholas Woodall
(74) *Attorney, Agent, or Firm* — Lerner, David, Littenberg, Krumholz & Mentlik, LLP (57) ABSTRACT

An osteonsynthesis implant has a plate-shaped base component having at least one hole, at least one axially extending rod-shaped tie rod having a first and a second end and at least one threaded component. The first end of the rod-shaped tie rod can be placed in the hole of the base component. The hole and the first end of the tie rod are formed such that the first end of the tie rod can be locked axially in the hole and is pivoted about an axis of the hole while locked to the plate. The second end of the tie rod is provided with a thread and the threaded component can be screwed onto the thread of the first tie rod. The tie rod can perform a pivoting movement of up to about 20° around the hole axis while locked in the plate hole.

11 Claims, 6 Drawing Sheets

U.S. PATENT DOCUMENTS

| | | |
|---|---|---|
| 2003/0125743 A1 | 7/2003 | Roman et al. |
| 2004/0210217 A1* | 10/2004 | Baynham et al. ............... 606/61 |
| 2004/0260291 A1 | 12/2004 | Jensen |
| 2005/0234472 A1 | 10/2005 | Huebner |
| 2006/0009771 A1 | 1/2006 | Orbay et al. |
| 2007/0088360 A1 | 4/2007 | Orbay et al. |
| 2007/0225715 A1 | 9/2007 | Deffenbaugh et al. |
| 2008/0210241 A1* | 9/2008 | Schulz et al. ............ 128/206.21 |

FOREIGN PATENT DOCUMENTS

| | | |
|---|---|---|
| DE | 9308944.9 | 8/1993 |
| DE | 19542064 | 6/1997 |
| EA | 0355035 | 2/1990 |
| EP | 1679044 | 7/2006 |
| JP | 2002-65682 | 3/2002 |
| WO | WO-99/09903 | 3/1999 |

* cited by examiner

DEVICE FOR CREATING A BONE IMPLANT

CROSS-REFERENCE TO RELATED APPLICATIONS

This application claims the benefit of the filing date of U.S. Provisional Patent Application No. 60/959,274 filed Jul. 11, 2007, the disclosure of which is hereby incorporated herein by reference.

BACKGROUND OF THE INVENTION

This invention relates to a device, particularly a kit for the production of an osteosynthesis implant.

Devices known as osteosynthesis or bone plates are commonly used for fracture fixation, generally with the possibility of a longitudinal adjustment of an osteotomy, as is known, for example, from DE 40 07 306 C and U.S. Pat. No. 5,129,903. In principle, with bone fractures there is a problem with fixing the bone parts together and precisely adjusting their location. With other indications, a bone is initially fractured in a targeted fashion, to subsequently fix the two bone parts together at their point of separation (osteotomy) at a fixed or variable distance so that the bone parts have the opportunity of growing together again.

The known osteosynthesis plates consist of two plate parts, longitudinally displaceable in relation to each other, that can be fixed to the bone parts, for example by means of bone screws. The mechanical guidance with the known osteosynthesis plates is provided by a dove tail guide members. An extracorporeally operable drive mechanism is provided in this area with which the plate parts can be displaced longitudinally to each other. In addition, the drive mechanism is formed such that a shaft, for example, is of a length and orientation such that it passes through the skin of the patient at only one single site after implantation in the patient's body. The shaft can then be operated from the outside using a suitable tool, for example, a screwdriver such that the osteotomy can be lengthened or shortened.

The known osteosynthesis plates sometimes do not provide satisfactory results, particularly when used in the jaw and skull area. Based on their design, the known osteosynthesis plates are spread relatively wide, i.e., their spatial depth is relatively large. This is attributable to the construction of the mechanical guide, for example as a dove tail guide. This can lead to difficulties with the implantation in the case of a spatially narrow area, as dictated by nature, at the implantation site.

With the osteosynthesis plate according to DE 195 42 064 C, an attempt is made to create a design that has significantly smaller dimensions so that it can be used at spatially narrow implantation sites, e.g., in the jaw or skull area.

Forming the mechanical guide from two cylindrical pins oriented in the direction of longitudinal displacement and formed from the first part of the plate and two cylindrical holes oriented in the direction of longitudinal displacement and provided in the second part of the plate has been proposed, where the pins are fitted into the holes.

The known osteosynthesis plates therefore are concerned primarily with the longitudinal displaceability of an osteotomy. They can be used on osteotomies or fractures of relatively large long bones. Use on smaller bones, for example, in the foot area, is practically impossible due to their still substantial overall size. In addition, they often create an unstable system, from the mechanical point of view, with unpredictable bending moments that can have a fatiguing effect on the material of the osteosynthesis plates and unpredictable forces that affect the bone screws used for fixing the plates.

SUMMARY OF THE INVENTION

The present invention can now be seen to relate, for one thing, to a device, particularly a kit, for the production of an osteosynthesis implant that overcomes the disadvantages in the current art.

The problem is solved through the subject of the independent claims, and advantageous embodiments are embodied in the dependent claims.

According to one aspect of the invention, a kit is proposed for the production of an osteosynthesis implant with a plate-shaped base component with at least two holes. At least two rod-shaped tie rods whose first end can be placed in the holes. The shape of the first end of the tie rods are formed such that the ends can be locked into the holes. When the tie rods are locked in the holes they can perform a pivoting movement. The tie rods have at least two threaded components that can be screwed together with second ends of the at least two tie rods being threaded. The second ends are each provided with one thread i.e. a male thread on one and a female thread on the other.

Such a device can also be used in the area of relatively small bones, for example in the area of the foot or hand, and, can represent a system in which the mechanical stresses can be predicted, so that fatigue breaks, etc., are not expected. The pivoting ability of the tie rods can play no further role in the implanted state if they are locked into the holes in the plate. The pivoting ability can, however, be a prerequisite for a tension-free implantation since it can permit the creation of holes in bones in varying directions, depending on the patient's individual situation which can be taken into consideration in situ by the surgeon. During the surgery, one can now proceed, for example, such that the plate-shaped base component is wedged under the osteotomy or fracture by means of tongs. Then the surgeon can create the holes in the bones depending on the actual conditions. Then the minimum of two tie rods whose second ends can be screwed together with the minimum of two threaded components can be placed in the holes in the bone from the other side of the bone. The lengths of the tie rods can be selected such that the first ends of the tie rods reach to the holes and can be used there. Further actuation of the threaded components can lead to the first end locking in the plate Once tightened the pivoting ability of the tie rod in situ in the holes is no longer required. Rather, it is a characteristic of the implant that can be created from the kit or the device prior to implantation.

The advantage to the device according to the invention can reside in the fact that angles of the bone holes can be adjusted to the individual patient, such that the plate-shaped base component and the tie rod, including the two threaded components, can be implanted without undesired additional tensile forces, bending moment, etc. Under certain circumstances, the plate-shaped base component can accept bending moments in only one direction, but this is defined and mechanically predictable. The tensile forces produced along the tie rod are desired since they can provide for a secure hold between the implant and the bone.

The osteosynthesis implant that can be produced from the device according to the invention is well suited for use in foot as well as hand surgery with narrowed spatial relations and small bones, but is not limited to this. While the implant according to the present invention is not preferred for use on large long bones, such as the femur or tibia, where a large number of greater stresses arise and where bending moments are expected in more than only one direction, the implant can be used on other bones, with the necessary adaptations.

According to an example of an embodiment, provision can be made for the tie rods, while locked into holes, to be able to perform a pivoting movement of up to 20° around the zero position in which the tie rods can stand perpendicular to the plate-shaped base component. This is in the delivery state and in the assembled state. As designed, this pivoting ability plays no further role under certain circumstances after implantation. The pivoting ability can be a prerequisite for tension-free implantation on the bones.

According to one aspect of the invention, provision can be made for the tie rods to be formed as a bushing and the thread components as screws.

According to one aspect of the invention, provision can be made, in a kinematic reversal, for the tie rods to be designed at their second ends as threaded spindles and for the thread components to be designed as bushes.

According to one aspect of the invention, provision can be made for the first ends of the tie rods to form a sort of bayonet closure with the holes in the plate-shaped base component. After rotation of the thread components screwed onto the second end of the tie rod, the first end of the tie rod can be locked into the holes. Further operation of the thread component can increase the tensile forces in the tie rod, which is desirable to a certain degree in order to stabilize the osteotomy or fracture.

According to one aspect of the invention, provision can be made for the surfaces of the base component facing the bone to have, at least in sections, an open-mesh, three-dimensional net structure. This open-meshed net structure can facilitate the ingrowth and intergrowth of bone material for long-term fixation.

According to an aspect of the invention, provision can be made for the surfaces of the thread components facing the bones to have, at least in part, an open-mesh, three-dimensional net structure, also for the creation of stable secondary fixation. In this case, for example, a second surgery is not scheduled to remove the implant after the fracture heals.

According to an aspect of the invention, the base component, tie rods and thread components can preferably be made of physiologically compatible metal.

According to an aspect of the invention, a device is prepared for production of an osteosynthesis implant with a plate-shaped base component; a first rod-shaped tie rod; and a first thread component; where the plate-shaped base component has a first hole; where the first rod-shaped tie rod has a first end and a second end; where the first rod-shaped tie rod with its first end can be placed in the first holes; where the first hole and the first end of the first tie rod are formed such that the first end can be locked into the first hole; where the first rod-shaped tie rod can perform a pivoting movement in the locked state; where the second end of the first tie rod is provided with a thread; and where the first thread component can be screwed on to the thread of the first tie rod.

According to an aspect of the invention, the device is provided with a second rod-shaped tie rod; and a second thread component; where the plate-shaped base component has a second hole; where the second rod-shaped tie rod has a first end and a second end; where the second rod-shaped tie rod with its first end can be placed in the second holes; where the second hole and the first end of the second tie rod are formed such that the first end of the second tie rod can be locked into the second hole; where the second rod-shaped tie rod can perform a pivoting movement in the locked state; where the second end of the second tie rod is provided with a thread; and where the second thread component can be screwed on to the thread of the second tie rod.

According to an aspect of the invention, at least one tie rod can perform a pivoting movement of 20° around the zero position, while locked in the related holes, in which position at least one tie rod is perpendicular to the plate-shaped base component.

According to one aspect of the invention, at least one of the tie rods has an internal thread and the related thread component has an external thread.

According to one aspect of the invention, at least one the tie rods has an external thread and the related thread component has an internal thread.

According to one aspect of the invention, a first end of at least one tie rod forms a type of bayonet closure with the corresponding hole in the plate-shaped base component.

According to one aspect of the invention, a surface of the base component facing a bone has, at least in sections, an open-meshed, three-dimensional net structure.

According to an aspect of the invention, a surface of at least one thread component facing a bone has, at least in part, an open-meshed, three-dimensional net structure.

According to an aspect of the invention, the base component has a greater material thickness in the area of at least one hole than in the areas that are away from the corresponding hole.

According to an aspect of the invention, the greater material thickness applies to one of the sides of the base component facing away from the bone.

According to an aspect of the invention, a device is prepared for production of an osteosynthesis implant with a plate-shaped base component; a first rod-shaped tie rod; and a first thread component; where the plate-shaped base component has a first hole; where the first rod-shaped tie rod has a first end and a second end; where the first rod-shaped tie rod with its first end can be placed in the first holes; where the first hole and the first end of the first tie rod are formed such that the first end can be locked into the first hole; where the first hole is provided with a deformable lip; where the first end of the first tie rod is provided with a first thread; where the first thread of the first tie rod can be brought, with positive and non-positive fit, into contact with the deformable lip of the first hole with the deformation of this deformable lip at least in sections; where the second end of the first tie rod is provided with a second thread; and where the first thread component can be screwed on the second thread of the first tie rod.

According to an aspect of the invention, a device is further prepared with a second rod-shaped tie rod; and a second thread component; where the plate-shaped base component has a second hole; where the second rod-shaped tie rod has a first end and a second end; where the second rod-shaped tie rod with its first end can be placed in the second holes; where the second hole and the first end of the second tie rod are formed such that the first end can be locked into the second hole; where the second hole is provided with a deformable lip; where the first end of the second tie rod is provided with a first thread; where the first thread of the second tie rod can be brought, with positive and non-positive fit, into contact with the deformable lip of the second hole with the deformation of this deformable lip, at least in sections; where the second end of the second tie rod is provided with a second thread; and where the second thread component can be screwed on the second thread of the second tie rod.

According to an aspect of the invention, at least one deformable lip has titanium or consists essentially of titanium. This lip can be segmented around its circumference so that it is easier to engage a thread. The lip can also have a plurality of coils in the direction of the depth of the hole so that there is a multiple lip arrangement. The lip segments can be rhombic or oval. The edges of the lip can be sharp edged or rounded off. The edges can be continuous or toothed.

According to an aspect of the invention, at least one of the tie rods has an internal thread and the related thread component has an external thread.

According to an aspect of the invention, at least one of the tie rods has an external thread and the related thread component has an internal thread.

According to an aspect of the invention, a first end 4 of at least one tie rod 3 forms a thread connection with the corresponding hole 2 in the plate-shaped base component 1, that facilitates a connection of a hole 2 of the base component 1 with a corresponding tie rod 3 at varying angles.

According to an aspect of the invention, a surface of the base component 1 facing a bone is provided, at least in sections, with an open-meshed, three-dimensional net structure.

According to an aspect of the invention, a surface of at least one thread component facing a bone is provided at least in part with an open-meshed, three-dimensional net structure.

According to an aspect of the invention, the base component, the tie rods and the thread components are made of physiologically compatible metal.

According to an aspect of the invention, the base or plate component has a greater material thickness in the area of the holes than in the areas away from a corresponding hole.

According to an aspect of the invention, the greater material thickness applies to a side of the base component facing away from the bone.

According to an aspect of the invention, a process is provided for the production of an osteosynthesis implant with a plate-shaped base component, a first and a second rod-shaped tie rod, and a first and second thread component, where the plate-shaped base component has a first and second hole, where the first and second rod-shaped tie rod each has a first end and a second end, and where each second end of the first and second tie rod is provided with a thread; Insertion of the first rod-shaped tie rod with its first end in the first hole; Locking of the first end of the first tie rod into the first hole; Insertion of the second rod-shaped tie rod with its first end into the second holes; locking of the first end of the second tie rod in the second hole; where the first and second rod-shaped tie ends in the locked state can perform a pivoting movement; Screwing of the first thread component onto the thread of the first tie rod; and screwing of the second thread component onto the thread of the second tie rod.

According to an aspect of the invention, a process is disclosed for the production of an osteosynthesis implant with a plate-shaped base component, a first and a second rod-shaped tie rod, and a first and second threaded component, where the plate-shaped base component has a first and second hole, where the first and second rod-shaped tie rod each has a first end and a second end, and where each second end of the first and second tie rod is provided with a thread, where the first and second hole has a deformable lip, where each first end of the first and second tie rod is provided with a thread and where each second end of the first and second tie rod is provided with a second thread; Insertion of the first rod-shaped tie rod with its first end into the first holes; locking of the first rod-shaped tie rod with its first end in the first hole; locking of the first end of the first tie rod in the first hole such that the first thread of the first tie rod is brought, with positive and non-positive fit, into contact with the deformable lip of the first hole with the deformation of this deformable lip at least in sections; Insertion of the second rod-shaped tie rod with its first end into the second hole; Insertion of the first end of the second tie rod in the second hole such that the first thread of the second tie rod is brought, with positive and non-positive fit, into contact with the deformable lip of the first hole with the deformation of this deformable lip at least in sections; Screwing of the first thread component onto the thread of the first tie rod; and screwing of the second thread component onto the thread of the second tie rod.

The individual characteristics described can of course be combined with each other, through which advantageous effects can also be created that exceed the total of the individual effects.

These aspects of the invention can be achieved by an osteosynthesis implant having a plate-shaped base component having at least a first hole; at least a first axially extending rod-shaped tie rod having a first and a second end and at least a first threaded component. The first end of the first rod-shaped tie rod can be placed in the first hole of the base component. The first hole and the first end of the first tie rod are formed such that the first end of the first tie rod can be locked axially in the first hole and is pivoted about an axis of the first hole while locked to the plate. The second end of the first tie rod is provided with a thread. The first threaded component can be screwed onto the thread of the first tie rod. A second rod-shaped tie rod and a second threaded component are provided and the plate-shaped base component has a second hole. The second rod-shaped tie rod has a first end and a second end where the second rod-shaped tie rod first end can be placed in the second holes. The second hole and the first end of the second tie rod are formed such that the first end of the second tie rod can be locked in the first hole. The second rod-shaped tie rod can perform a pivoting movement in the locked state. The second end of the second tie rod is provided with a thread and the second thread component can be screwed onto the thread of the second tie rod.

The tie rod can perform a pivoting movement of up to about 20° around the hole axis while locked in the plate hole. The tie rod preferably has an internal thread and the related threaded component has an external thread. The tie rod has an external thread and the related threaded component has an internal thread. A first end of the tie rod may form a type of bayonet closure with the corresponding hole in the plate-shaped base component. A surface of the plate-shaped base component facing the bone can include an open-meshed, three-dimensional net structure. A surface of the threaded component facing a bone can also have an open-meshed, three-dimensional net structure. The plate-shaped base component, the tie rod and the threaded component are made of bio-compatible metal.

The plate-shaped base component has a greater material thickness in the area of the hole than in an area away from the hole. The greater material thickness applies to a side of the base component facing away from the bone.

Aspects of the invention are accomplished by an osteosynthesis implant including a plate-shaped base component having at least a first hole, a first rod-shaped tie rod having a first and a second end, and a first threaded component. The first rod-shaped tie rod first end can be placed in the first hole. The first hole and the first end of the first tie rod are formed such that the first end of the first tie rod can be locked in the first hole. The first hole has a deformable lip and the first end of the first tie rod is provided with a thread where the first thread component of the first tie rod can be brought into contact with the deformable lip of the first hole with at least partially deforming the deformable lip. The second end of the first tie rod is provided with a second thread. The first thread component can be screwed onto the second thread of the first tie rod.

The implant may further comprise a second rod-shaped tie rod and a second threaded component and the plate-shaped base component has a second hole. The second rod-shaped tie rod has a first end and a second end where the second rod-shaped tie rod with its first end can be placed in the second hole. The second hole and the first end of the second tie rod are formed such that the first end of the second tie rod can be locked in the second hole. The second hole has a deformable lip where the first end of the second tie rod is provided with a thread and where the first thread component of the second tie rod can be brought, with positive and non-positive fit, into contact with the deformable lip of the second hole at least partially deforming the deformable lip. The second end of the second tie rod is provided with a second thread. The second thread component can be screwed onto the second thread of the second tie rod. The deformable lip may be titanium or titanium alloy.

Another aspect of the invention relates to a method for implanting an osteosynthesis implant which includes providing an osteosynthesis implant including a plate-shaped base component, a first and second axially extending rod-shaped tie rod, and a first and second threaded component. The plate-shaped base element has a first and a second hole, where the first and the second rod-shaped tie rod each has a first end and a second end, and where each second end of the first and the second tie rod is provided with a thread. The first end of the first rod-shaped tie rod is inserted into the first base component hole. The first end of the first tie rod is locked in the first hole in the axial direction. The first end of the second rod-shaped tie rod is inserted in the second base component hole. The first end of the second tie rod is axially locked into the second hole. The first and the second rod-shaped tie rods may be pivoted in the axially locked state. The first thread component is screwed onto the thread of the first tie rod and the second thread component is screwed onto the thread of the second tie rod. A deformable lip may be provided, where the first end of each of the first and second tie rods are provided with a thread and where each second end of the first and second tie rod is provided with a second thread. The first rod-shaped tie rod is inserted with its first end into the first holes and locked. The first thread of the first tie rod is brought, with positive and non-positive fit, into contact with the deformable lip of the first hole at least partially deforming the lip.

BRIEF DESCRIPTION OF THE DRAWINGS

These and other aspects of this invention are explained and elaborated through reference to the embodiments described as examples below. Examples of embodiments are described in the following with reference to the following drawings. They show.

DETAILED DESCRIPTION

Figure 1:
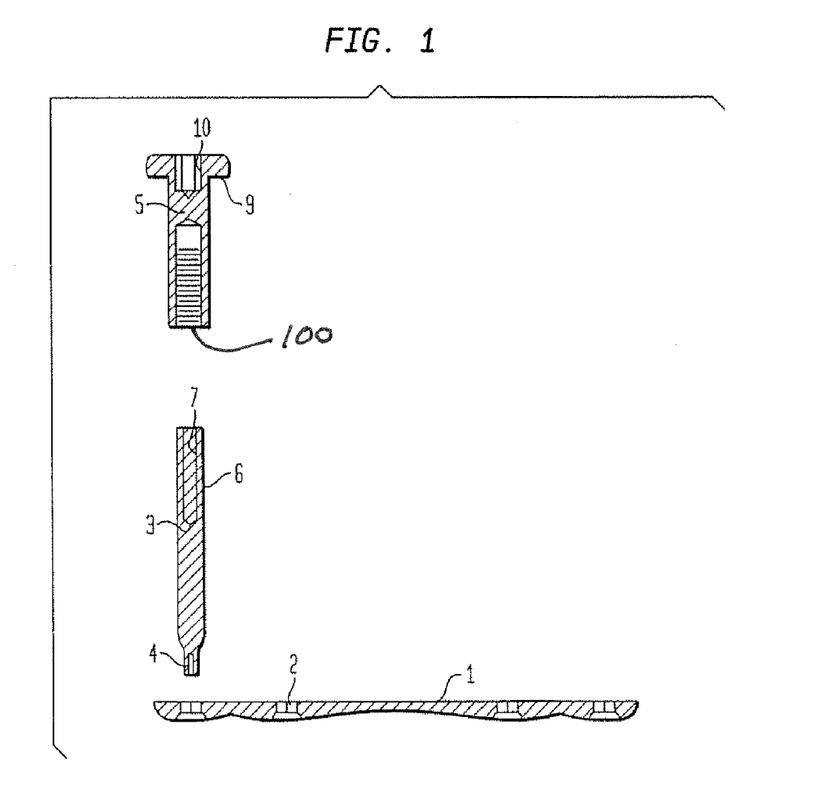
FIG. 1 is a cross-section view through an example of an embodiment of the three components of the set.

FIG. 1 shows a schematic cross-section through all three components of the system according to an example of the invention. The plate-shaped base component 1 has at least two holes 2, and preferably four holes. In each of the holes 2, a tie rod 3 can be placed with its first end 4 engaging hole 2. The second end 7 of the tie rod 3 is provided, with a thread 6. A threaded component 5 preferably in the form of a bushing with a female thread 100 can be screwed onto the threaded end 7 of tie rod 3. A tool attachment 10 is provided in a head 10A, for example a hexagon socket.

Figure 2:
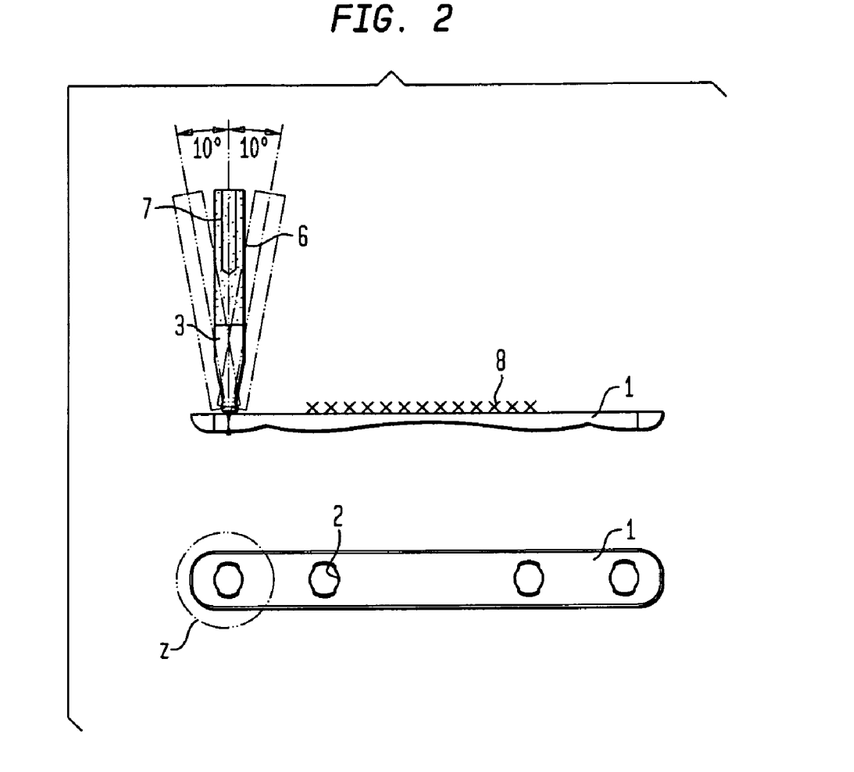
FIG. 2 is a schematic view of an example of an embodiment of a base component with a tie rod.

The distinctive feature about the connection between tie rod 3 and the base component 1 is shown in FIG. 2 according to a preferred embodiment of the invention. A first end 4 of tie rod 3 is placed in hole 2 in base plate component 1. The hole 2 and the first end 4 of tie rod 3 are designed such that the end 4 can be locked into hole 2, where tie rod 3 can, in the axially locked position, performed a pivoting movement, as shown by the dotted line of tie rod 3 in FIG. 2, where a pivot movement of 10° around the zero position is shown, i.e., the position in which tie rod 3 is perpendicular to plate-shaped base component 1. This pivoting movement comes to bear only indirectly in the implantation, as explained in greater detail below in relation to FIG. 5.

The surface of the base component 1 facing the bone is, according to one embodiment of the invention presented here in cross-section, an open-meshed, three-dimensional net structure 8 in which and through which the bone trabecula organizes and grows and thus ensures a lasting secondary fixation. A comparable structure is shown here on the surface of thread component 5 facing the bone in FIG. 1.

Figure 3:
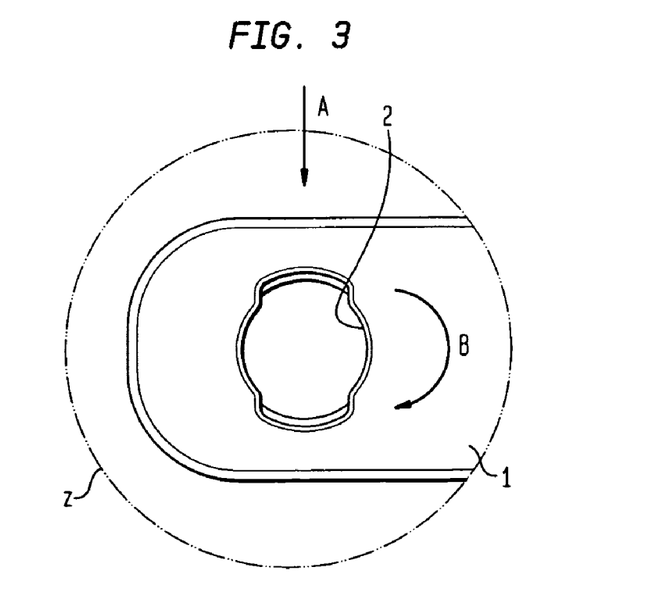
FIG. 3 is a view of an example of an embodiment of a plate-shaped base component and the enlargement of detail Z.

FIG. 3 shows a view of plate-shaped base component 1 according to an embodiment of the invention with four holes 2. Furthermore, the enlarged detail Z is to be noted which shows a special contour for the holes 2. This is necessary according to a preferred embodiment of the invention to permit axial locking between the plate and tie rod 3, on the one hand, and on the other hand, to allow a certain degree of pivoting movement despite the axial locking. Arrow A shows the direction of use of the first end 4 of a tie rod 3 in the hole 2 with locking. Arrow B then indicates the movement of the tie rod 3 in the hole 2 during locking. Here, the first ends 4 of the tie rod 3 together with the holes 2 form a bayonet closure according to one example of embodiment of the invention. Thus, the end 4 of tie rod 3 is inserted in hole 2 and rotated a quarter turn to cyclically lock the tie rod in hole 2.

Figure 4:
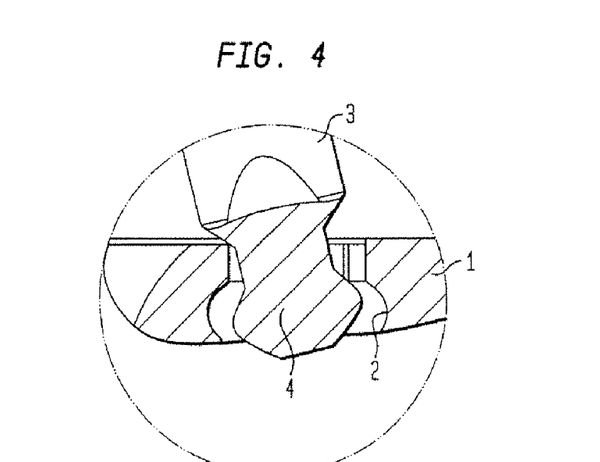
FIG. 4 is an enlarged cross-section view through an example of an embodiment of the base component in the area of one of the holes with the tie rod inserted and locked.

The pivoting ability of the first end 4 of the tie rod 3 in the hole 2 in the base component 1 is indicated in FIG. 4. Despite the positive fit against further rotation in the locked state, it is possible, according to an example of embodiment of the invention, to pivot the tie rod 3 in the hole 2, as indicated in FIG. 2.

Figure 5:
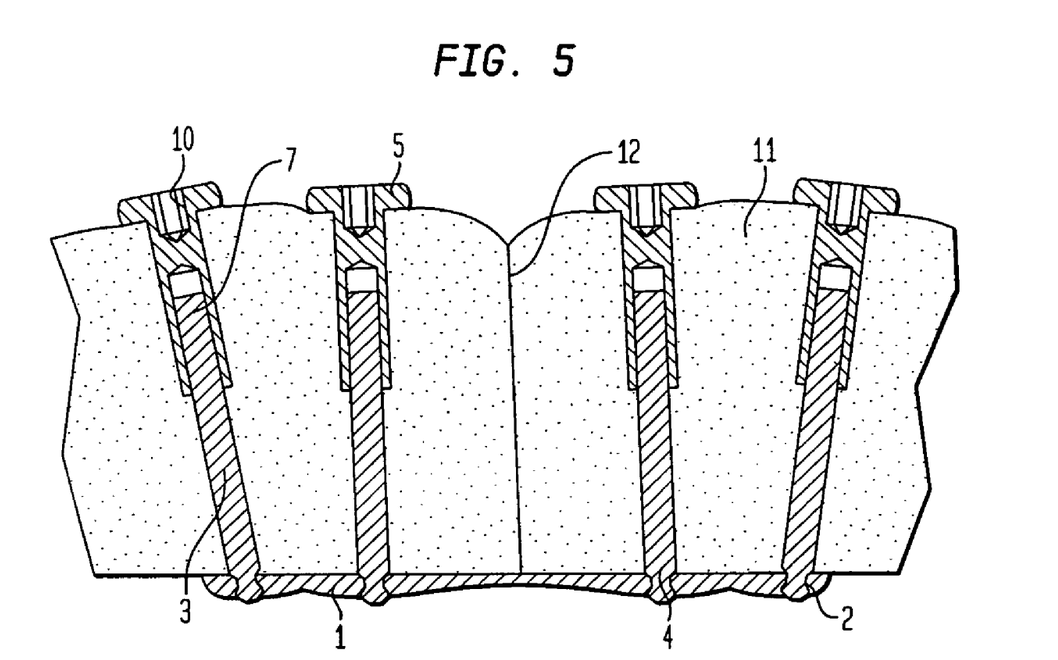
FIG. 5 is a schematic view of an example of an embodiment of the osteosynthesis implant prepared from the set, after implantation.

The mechanism of action of the set or the osteosynthesis implant created from it is shown in FIG. 5. It shows a cross-section of the osteosynthesis implant located on the bone 11 to stabilize the fracture 12.

The four hole base component 1, lies to one side of the bone 11 to be stabilized. It is then wedged there with tongs (not shown). In this position, it serves as a hole template to create the four holes here in the bone, at different angles, depending on the shapes and distinctive characteristics of the bone. After creation of the holes in bone 11, the unit composed of the tie rod 3 and the thread component 5 screwed onto it is placed in the respective hole in the bone until its first end comes into the area of hole 2 in the base component 1. A further rotation of the threaded component 5 leads to the locking of the tie rod 3 in the hole 2. It is reasonable that the pivoting ability of the tie rod 3 in the hole 2, explained above in greater detail, is a prerequisite for the insertion of the tie rods 3 into the holes with different orientations during implantation.

The result is a tension-free seat for the implant in and on the bone 11 so that no additional stresses that could not be known in advance are introduced to the bone 11 and the stresses also do not affect the implant. A further rotation of the thread component 5 leads to an increase of the tensile forces in the tie rods 3, which can lead to a greater stabilization of the fracture 12.

The base component 1, the tie rods 3 and the thread component 5 are preferably made of a physiologically compatible metal to be able to withstand the resultant stresses, for example, such as stainless steel or titanium.

Figure 6A:
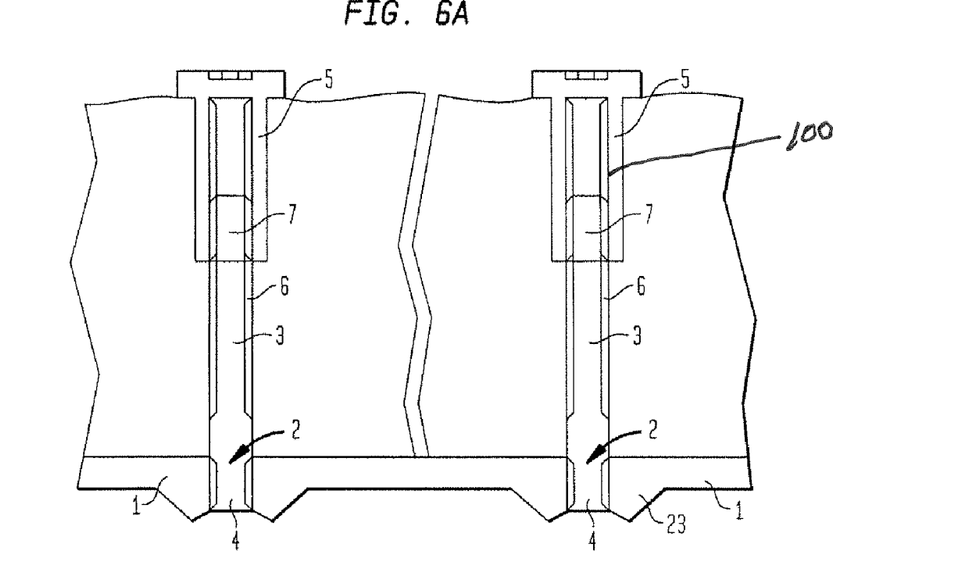
FIG. 6*a* is a schematic view of an example of an embodiment with a coating.

FIG. 6a shows an arrangement according to a second embodiment of the invention in which a device for production of an osteosynthesis implant is provided with a plate-shaped base component 1, a first rod-shaped tie rod 3 and a first thread component 5. The plate-shaped base component 1 has a first hole 2. The first rod-shaped tie rod 3 has a first end 4 and a second end 7, where the first rod-shaped tie rod with its end 4 can be placed in the first hole 2. The first hole 2 and the first end 4 of the first tie rod 3 are formed such that the first end 4 can be locked into the first hole 2. In the first hole 2, a deformable lip 21 is provided. The first end 4 of the first tie rod 3 is provided with a first thread 22, where the first thread 22 of the first tie rod 3 can be brought, with positive and non-positive fit, into contact with the deformable lip 21 of the first hole 2 under deformation of this deformable lip 21 at least in sections. The second end 7 of the first tie rod 3 is provided with a second thread 6 where the first thread component 5 can be screwed onto the second thread 6 of the first tie rod 3.

According to a further embodiment of the invention, the device has a second rod-shaped tie rod 3 and a second threaded component 5. The plate-shaped base component 1 has, according to an example of embodiment of the invention, a second hole 2. The second rod-shaped tie rod 3 has, according to an example of embodiment of the invention, a first end 4 and a second end 7, where the second rod-shaped tie rod with its first end 4 can be placed in the second holes 2. The second hole 2 and the first end 4 of the second tie rod 3 are, according to an example of embodiment of the invention, formed such that the first end 4 of the second tie rod 3 can be locked into the second hole 2. A deformable lip 21 is provided in the second hole 2, according to an example of embodiment of the invention. The first end 4 of the second tie rod 3 can be provided with a first thread 22, where the first thread 22 of the second tie rod 3 can be brought, with positive and non-positive fit, into contact with the deformable lip 21 of the second hole 2 under deformation of this deformable lip, at least in sections, where the second end 7 of the second tie rod 3 can be provided with a second thread 6. The second thread component 5, according to an example of embodiment of the invention, can be screwed onto the second thread 6 of the second tie rod 3.

According to one embodiment of the invention, at least one of the deformable lips 21 has titanium or is made essentially from titanium. Titanium is a particularly light and stable material that is also very well tolerated by the human body.

According to another embodiment of the invention, a first end 4 of at least one tie rod 3 is formed, with the corresponding hole 2 in the plate-shaped base component 1, as a thread component that enables a connection of hole 2 of the base component 1 with a corresponding tie rod 3 at various angles.

A screw head can, for example, be provided with a hexagonal recess so that a tool can be inserted for secure fastening. Due to an increased material thickness 23 in the area of the hole 2, an enlarge hole depth can be created for the thread connection without having to significantly increase the weight of the entire implant there.

Figure 6B:
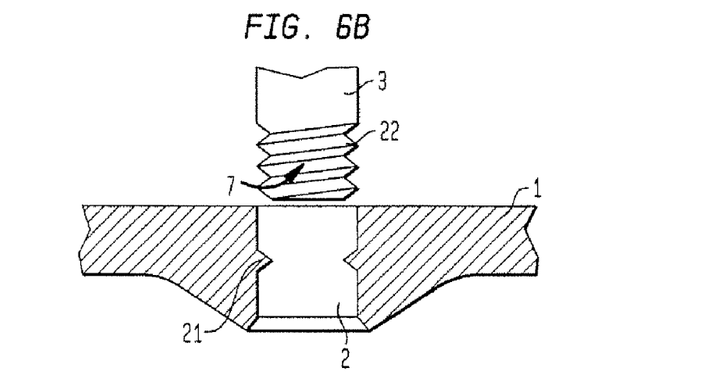
FIG. 6*b* is an example of an embodiment of a lip in undeformed condition without the thread applied.
Figure 6C:
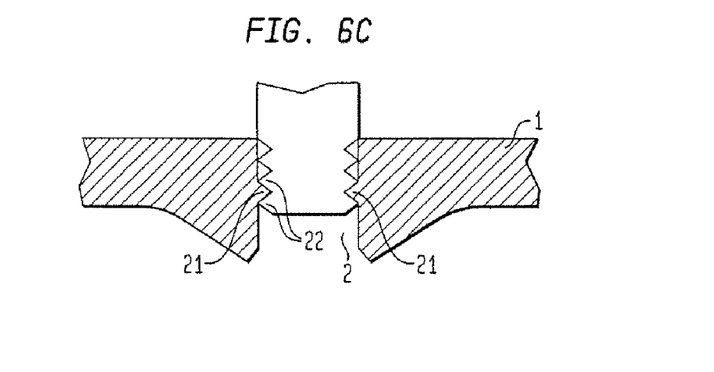
FIG. 6*c* is an example of an embodiment of a lip in deformed condition with the thread applied.

FIG. 6b shows a hole 2 with a lip 21 where the lip is not yet deformed by the insertion of a thread 22. FIG. 6c shows the thread 22 screwed into the hole 2 where the lip 21 undergoes deformation due to the insertion of the thread 22, which creates both a non-positive and a positive fit connection between the thread 22 and the lip 21 in hole 21.

Figure 7:
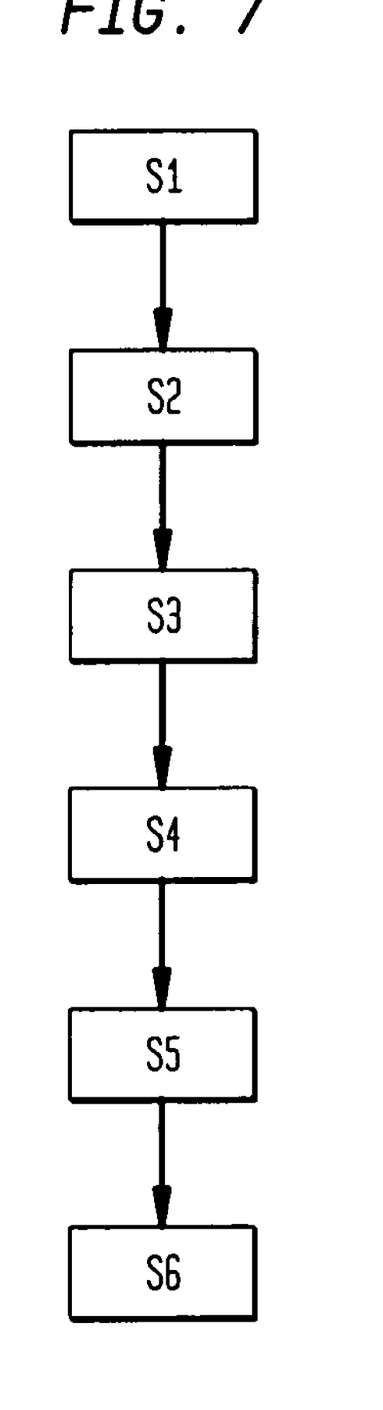
FIG. 7 is a schematic view of the flow of a process according to an example of an embodiment of the invention.

FIG. 7 shows a process used to create an osteosynthesis implant. S1 is the preparation of an osteosynthesis implant with a plate-shaped base component, a first and a second rod-shaped tie rod, and a first and a thread component, where the plate-shaped base element has a first and a second hole, where the first and the second rod-shaped tie rod each have a first end and a second end, and where each second end of the first and the second tie rod is provided with a thread; S2 is the insertion of the first rod-shaped tie rod with its first end into the first holes; S3 is the locking of the first end of the first tie rod in the first hole; S4 is the insertion of the second rod-shaped tie rod with its first end in the second holes; S5 is the locking of the first end of the second tie rod into the second hole; where the first and the second rod-shaped tie rod can perform a pivoting movement in the locked state; S7 is the screwing of the first thread component onto the thread of the first tie rod; and screwing of the second thread component onto the thread of the second tie rod.

Figure 8:
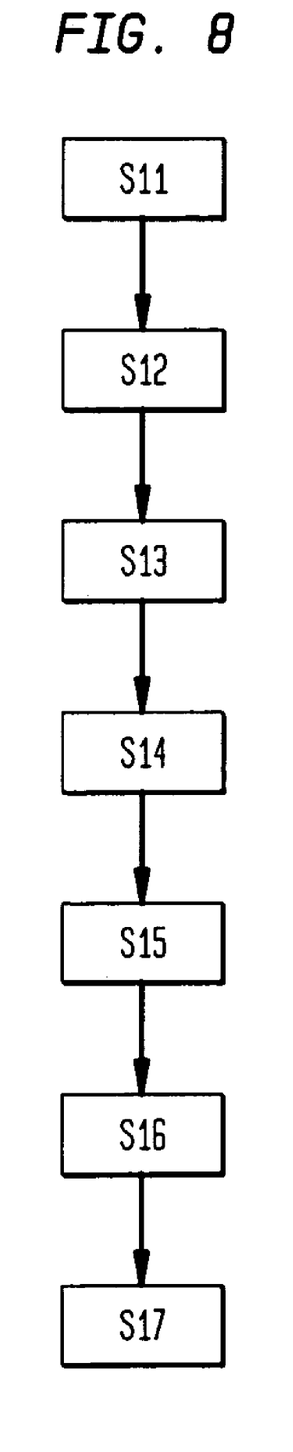
FIG. 8 is a schematic view of the flow of a process according to another example of an embodiment of the invention.

FIG. 8 shows an example of an embodiment of a process for the production of an osteosynthesis implant. S11 is the preparation of an osteosynthesis implant with a plate-shaped base component, a first and a second rod-shaped tie rod, and a first and a thread component, where the plate-shaped base component has a first and a second hole, where the first and the second rod-shaped tie rod each has a first end and a second end, and where each second end of the first and second tie rod is provided with a thread, where in the first and second hole a deformable lip is provided, where the first end of each of the first and second tie rods is provided with a thread and where each second end of the first and second tie rod is provided with a second thread; S12 is the insertion of the first rod-shaped tie rod with its first end into the first holes; S13 is the locking of the first end of the first tie rod in the first hole such that the first thread of the first tie rod is brought, with positive and non-positive fit, into contact with the deformable lip of the first hole with deformation of this deformable lip at least in sections; S14 is the insertion of the second rod-shaped tie rod with its first end of the second holes; S15 is the locking of the first end of the second tie rod in the second hole such that the first thread of the second tie rod is brought, with positive and non-positive fit, into contact with the deformable lip of the second hole, with deformation of this deformable lip, at least in sections; S16 is the screwing of the first thread component onto the thread of the first tie rod; and S17 is the screwing of the second thread component onto the thread of the second tie rod.

Note that the steps in the process can also be carried out, to the extent expedient, in a different sequence.

Note that the term "comprise" does not exclude additional components or process steps; similarly, the terms "a" and "one" does not exclude a plurality of components and steps. The reference numbers used serve solely to increase comprehensibility and should not, in any way, be considered limitative, where the scope of protection of the invention is reproduced in the Claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An osteonsynthesis implant comprising:
    a plate-shaped base component having at least a first hole, the first hole having first opposite circular segments connected by two arcuate sections having a larger diameter centered at 90° from each circular segment;
    at least a first axially extending rod-shaped tie rod having a first and a second end;
    at least a first threaded component;
    the first end of the first rod-shaped tie rod can be placed in the first hole of the base component;
    where the first hole and the first end of the first tie rod are formed such that the first end of the first tie rod can be locked axially in the first hole and is pivoted about an axis of the first hole while locked to the plate up to about 20° around the axis of the first hole;
    wherein the second end of the first tie rod is provided with a thread; and
    where the first threaded component can be screwed onto the thread of the first tie rod and wherein the first end of the first tie rod can be locked in the first hole and pivoted with the first threaded component screwed onto the first tie rod.

2. The implant of claim 1, further comprising:
    a second rod-shaped tie rod; and
    a second threaded component;
    where the plate-shaped base component has a second hole;
    where the second rod-shaped tie rod has a first end and a second end;
    where the second rod-shaped tie rod first end can be placed in the second hole;
    where the second hole and the first end of the second tie rod are formed such that the first end of the second tie rod can be locked in the second hole;
    where the second rod-shaped tie rod can perform a pivoting movement in the locked state;
    where the second end of the second tie rod is provided with a thread; and
    where the second thread component can be screwed onto the thread of the second tie rod.

3. The implant of claim 1 wherein the tie rod has an internal thread and the related threaded component has an external thread.

4. The implant of claim 1 wherein the tie rod has an external thread and the related threaded component has an internal thread.

5. The implant of claim 1 wherein a first end of the tie rod forms a type of bayonet closure with the corresponding hole in the plate-shaped base component.

6. The implant of claim 1 wherein a surface of the plate-shaped base component facing the bone has an open-meshed, three-dimensional net structure.

7. The implant of claim 1 wherein a surface of the threaded component facing a bone has an open-meshed, three-dimensional net structure.

8. The implant of claim 1 wherein the plate-shaped base component, the tie rod and the threaded component are made of bio-compatible metal.

9. The implant of claim 1 wherein the plate-shaped base component has a greater material thickness in the area of the hole than in an area away from the hole.

10. The implant of claim 9 wherein the greater material thickness applies to a side of the base component facing away from the bone.

11. An apparatus configured to fasten an osteosynthesis implant, comprising:
    a base plate element having a first attachment hole, the first attachment hole having first opposite circular segments connected by two arcuate sections having a larger diameter centered at 90° from each circular segment;
    a first anchor bolt having an upper and lower end, the upper end having a threaded portion; and
    a first threaded fastening bolt, the threaded fastening bolt configured to threadably engage with the threaded portion of the first anchor bolt;
    wherein the lower end of the first anchor bolt and the first attachment hole of the base plate element has a complementary shape to engage and fasten with each other in at least one rotational position of the first anchor bolt with the tip thereof inserted through the hole, and are configured to allow a swivel action of the first anchor bolt while engaged to the first threaded anchor bolt when the first anchor bolt is fastened in the base plate element hole up to an angle of 20° with an axis of the first attachment hole.

* * * * *